United States Patent [19]

Schwartz

[11] Patent Number: 4,960,905

[45] Date of Patent: Oct. 2, 1990

[54] PHENOXY PHTHALIC ANHYDRIDES

[75] Inventor: Willis T. Schwartz, Grand Island, N.Y.

[73] Assignee: Occidental Chemical Corporation, Niagara Falls, N.Y.

[21] Appl. No.: 284,639

[22] Filed: Dec. 15, 1988

Related U.S. Application Data

[62] Division of Ser. No. 98,813, Sep. 21, 1987, Pat. No. 4,827,000.

[51] Int. Cl.$^5$ ............................................. C07D 307/89
[52] U.S. Cl. .................................................... 549/243
[58] Field of Search ......................................... 549/243

[56] References Cited

U.S. PATENT DOCUMENTS 3,850,965  11/1974  Williams ........................ 549/243 X

FOREIGN PATENT DOCUMENTS 2182328  5/1987  United Kingdom .

OTHER PUBLICATIONS

Rolles et al., Chemical Abstracts, vol. 92 (1980), 180497y.
Haddock et al., Chemical Abstracts, vol. 104 (1986), 50785w.

Primary Examiner—Richard L. Raymond
Attorney, Agent, or Firm—James F. Tao; Arthur S. Cookfair

[57] ABSTRACT

Phenoxy phthalic anhydrides are prepared by the reaction of a fluorophthalic anhydride with a phenol compound in the presence of potassium fluoride and a polar, aprotic solvent.

17 Claims, No Drawings

PHENOXY PHTHALIC ANHYDRIDES

This is a division of application Ser. No. 098,813, filed Sept. 21, 1987, now U.S. Pat. No. 4,827,000.

BACKGROUND OF THE INVENTION

This invention relates to a method for the preparation of substituted ether phthalic anhydrides. The products are useful chemical intermediates for the further preparation of various compounds such as the corresponding di-carboxylic acids and the various derivatives thereof, including for example, the salts, esters, acyl halides, amides, imides and the like. The ether phthalic anhydrides are useful as curing agents for epoxy resins and the like, and as monomers in the preparation of polyesters, for example by polycondensation with a suitable dihydric alcohol.

Various methods for the preparation of ether phthalic anhydrides have been described in the chemical literature. The preparation of diether-diphthalic anhydrides by formation of the diether di-o-xylyl groups followed by oxidation to the diether diphthalic anhydride is disclosed by Koton et al, Zh. Org. Khim. 4, 774 (1968); and Zh. Org. Khim. 6, 88 (1970).

Myers (U.S. Pat. No. 3,965,125) teaches the preparation of halogenated phthalimides from halogenated phthalic anhydride and reaction of the phthalimide with an alkaline metal salt of a phenol or a diphenol to form the bis-ether imide which is then hydrolyzed, acidified, and dehydrated to the bis-ether phthalic anhydride.

Heath et al (U.S. Pat. No. 3,956,320) disclose the preparation of aromatic bis(ether anhydride) by reaction of a nitro-substituted phenyl dinitrile with a metal salt of a dihydroxy aryl compound in the absence of a dipolar aprotic solvent and conversion of the resultant aryloxy tetranitrile to the tetra-acid followed by dehydration to the aryloxy dianhydride. Thus, for example, the patentees disclose the reaction of hydroquinone with 4-nitrophthalonitrile in the presence of potassium carbonate, followed by hydrolysis, acidification and dehydration to form the hydroquinone di-ether phthalic anhydride.

Johnson et al (U.S. Pat. No. 4,020,069) teach the reaction of a 4-nitro-N-alkyl phthalimide and an aromatic dihydroxy compound in the presence of potassium carbonate and dimethyl sulfoxide followed by hydrolysis to form a bis-ether dicarboxylic acid which may then be dehydrated to form the aromatic ether dianhydride.

Williams (U.S. Pat. No. 3,850,965) discloses a method for the preparation of aromatic ether anhydrides by reaction of a nitro- or halo-substituted aromatic anhydride with an alkali phenoxide. Thus, for example, sodium phenoxide was reacted with 3-fluorophthalic anhydride in anhydrous dimethylformamide to form 3-phenoxyphthalic anhydride.

Heath et al (U.S. Pat. No. 3,787,475) disclose the preparation of aryloxy phthalic acids by reaction of a metal phenolate such as sodium phenolate and a nitro ester of a phthalic acid such as diethyl-4-nitrophthalate or a corresponding nitrophthalonitrile, followed by hydrolysis of the ester group or cyano group. The resulting substituted phthalic acid may then be converted to the anhydride.

Williams (U.S. Pat. No. 3,850,964) discloses a method for making aromatic bis(ether anhydrides) by reaction of alkali metal diphenoxides with halo- or nitro-substituted aromatic anhydrides. Thus, for example, a sodium salt of 4,4'-dihydroxy biphenol was reacted with 3-fluorophthalic anhydride in anhydrous dimethyl formamide to form 2,2-bis[4-(2,3-dicarboxyphenoxy)-phenyl]propane dianhydride.

Markezich (U.S. Pat. No. 3,992,407) discloses the preparation of aromatic bisimides by reaction of a 3- or 4-fluoro-N-substituted phthalimide with an aromatic dihydroxy compound in the presence of a solid alkali metal fluoride, such as potassium fluoride, using a dipolar aprotic solvent.

SUMMARY OF THE INVENTION

In accordance with the present invention there is provided a process for the preparation of ether phthalic anhydrides of the formula

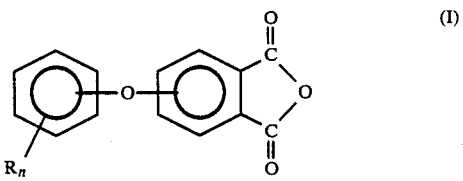

wherein each R is independently hydrogen, halogen, alkyl, substituted alkyl, alkoxy, substituted alkoxy, carboalkoxy, substituted carboalkoxy, carboaryloxy, substituted carboaryloxy, cyano, nitro, acetamido, aldehyde, tertiary amino, aryl, substituted aryl, aryloxy, substituted aryloxy, aroyl, or substituted aroyl, alkaryl, such as benzyl, substituted alkaryl, or two R's may be combined to form a fused ring; and n is 1–3; which comprises reacting a fluorophthalic anhydride of the formula

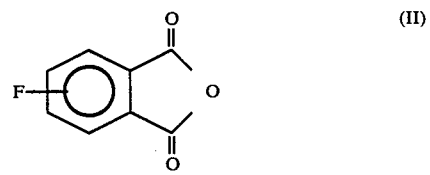

with a phenol compound of the formula

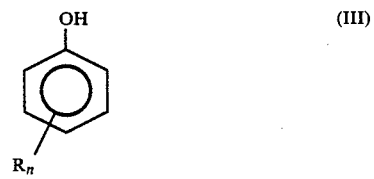

where R and n are as defined above, in the presence of potassium fluoride or cesium fluoride or a mixture thereof, and a polar aprotic solvent.

The R substituent in the phenol reactant (III) and in the ether phthalic anhydride (I) prepared in accordance with this invention, may be selected from a wide variety of substituted or unsubstituted organic radicals or inorganic atoms or radicals that do not interfere with the formation of the ether bridge that characterizes the product. When R is substituted alkyl, alkoxy, carboalkoxy, carboaryloxy, aryl, aryloxy, aroyl, alkaryl or the like, the substituents thereon may be, for example, halogen, alkyl, cyano, nitro, or the like. Preferred phenol reactants are those wherein the R substituent is hydrogen, alkyl or alkoxy of 1 to 10 carbon atoms, halo-substituted alkyl or alkoxy, especially trifluoromethyl or trifluoromethoxy, phenyl, chlorophenyl, cyano, nitro, acetamido, chlorine, fluorine, bromine and n is 1 or 2. It will be appreciated by those skilled in the art that, in some instances, the spatial volume or arrangement of atoms or groups near the phenolic reactive site (especially the 2- and 6- positions on the phenol molecule) may retard or prevent the desired reaction. Examples of this effect, commonly referred to as steric hindrance, can be seen in the experimental data presented hereinbelow. Thus, for example, the attempted reaction of 2,6-di-t-butyl phenol with 4-fluorophthalic anhydride (Example 34) was unsuccessful due to steric hindrance. However, in a similar reaction, except that 2,6-di-isopropyl phenol was employed (Example 36), the smaller alkyl substituent provided less steric hindrance, with the result that 4-(-2,6-di-isopropyl phenoxy) phthalic anhydride was produced in 18 percent yield. Furthermore, when a phenol reactant having a t-butyl substituent at only one site adjacent to the reactive hydroxyl was employed (Example 33) a 28 percent yield of the desired product was obtained. Additional examples of steric effects in the process of this invention, can be seen in the reactions involving 2,6-dihalophenols. See Examples 26, 28 and 29, where, as the atomic radius of the halogen substituent decreases from bromo- to chloro- to fluoro-, the yield of desired product increases, from 12.4 to 27.0 to 70.2 percent, respectively. Moreover, a comparison of the reactivity of difluorophenols of Examples 26 and 27 demonstrates a decrease in steric hindrance when one of the fluorine atoms is positioned further from the reactive site.

Representative phenolic compounds that may be employed in the process of the invention include compounds and isomers thereof, such as: phenol; nitrophenol; cyanophenol; trifluoromethylphenol; bromophenol; fluorophenol; chlorophenol; difluorophenol; dichlorophenol; acetamidophenol; methoxyphenol; ethoxyphenol; diethoxyphenol; cresol; dimethylphenol; hydroxydiphenyl; p-hydroxyacetophenone; thymol; naphthol; phenanthrol, and the like.

The proportions of fluorophthalic anhydride and phenolic compound provided to the reaction mixture may vary considerably from the stoichiometric ratio with either being employed as a limiting reactant. It may be economically advantageous to employ a stoichiometric excess, such as about 10 percent excess, of the least expensive reactant.

The fluorophthalic anhydride reactant may be either 3-fluoro-or 4-fluorophthalic anhydride or a mixture thereof and may be provided as an initial component of the reaction mixture or may be formed in-situ by the reaction of a bromo-, chloro-, or iodo-phthalic anhydride with KF. In the process of the invention, the fluorine atom on the fluorophthalic anhydride reactant functions as a leaving group and becomes the site for the formation of the ether bridge.

The process of the invention is preferably carried out at atmospheric pressure, but super-atmospheric pressure, for example under autogeneous conditions may be employed, if desired. The process is preferably carried out in the presence of a polar, aprotic solvent such as N-methyl-pyrrolidone, dimethyl formamide, dimethyl acetamide, triglyme, sulfolane, or the like.

The temperature at which the process is carried out may vary considerably, but will generally be within the range of about 120° to about 220° Celsius. Higher or lower temperature may be employed but are generally less efficient. The choice of solvent may govern the temperature employed. For example, at atmospheric conditions the boiling point of the solvent becomes a limiting condition. The preferred temperature is in the range of about 140° to 210°.

The proportions of alkali metal fluoride reactant employed may vary considerably. However, it is recommended that the alkali metal fluoride be employed in sufficient proportions to provide at least about one equivalent of potassium (or cesium) per mole of fluorophthalic anhydride. In the reaction, the alkali metal fluoride functions as a hydrogen fluoride acceptor. When the fluorophthalic anhydride reactant is to be formed in-situ from an initial mixture of chlorophthalic anhydride, bromophthalic anhydride or iodophthalic anhydride, it is preferred to provide at least about two equivalents of alkali metal fluoride per mole of chloro- or bromo- or iodophthalic anhydride. Preferably the alkali metal compound is employed in substantial excess, for example, up to about 50 percent excess, of the aforesaid equivalent proportions.

The ether phthalic anhydrides (Formula I) prepared in accordance with this invention can be employed as monomers in the further preparation of polyesters by reaction with a suitable dihydric alcohol, such as ethylene glycol, using known chemistry. The anhydride may be employed as the sole anhydride (dicarboxylic acid) reactant or in combination with other dicarboxylic anhydrides (dicarboxylic acids) in a ratio selected to give the desired properties. Anhydrides possessing ethylenic unsaturation may be employed to generate thermoset resins. The molar ratio of dihydric alcohol to dicarboxylic acid should be 1:1 if the highest molecular weight is desired, but can be adjusted in a known manner to provide a molecular weight range preferred for a specific application.

The ether phthalic anhydrides of this invention may be employed as epoxy curing agents in a known manner either individually or in combination or in combination with various known anhydride curing agents, such as NADIC methyl anhydride, 3,3',4,4'-benzophenone tetracarboxylic dianhydride, methyl tetrahydrophthalic anhydride, chlorendic anhydride, hexahydrophthalic anhydride and the like. As is known, the amounts of anhydride curing agent employed will depend on the epoxy equivalent weight. Thus, for example, one hundred parts of EPON 828 (Shell Chemical Company), having an epoxy equivalent weight of 185-192, may be cured by mixing with about 150 parts of trifluoromethylphenoxy phthalic anhydride. Epoxy resins employing such curing agents are particularly useful for electronic applications, for example, as encapsulants, laminates, coatings, fiber reinforced composites, casting resins and the like.

Furthermore, since the ether anhydrides of this invention are monoanhydrides, they are useful as chain stoppers in the preparation of polyimides, to control molecular weight.

The following examples are provided to further illustrate this invention and the manner in which it may be carried out. It will be understood, however, that the specific details given in the examples have been chosen for purposes of illustration only and are not to be construed as limiting the invention. In the examples, unless otherwise indicated, all parts and percentages are by weight and all temperatures are in degrees Celsius.

EXAMPLE 1

A mixture of 21.0 parts of 4-nitrophenol, 25.0 parts of 4-fluorophthalic anhydride, and 10.5 parts of potassium fluoride in 126 parts of sulfolane, was heated and maintained at a temperature of about 206°–209° C., with stirring, over a period of about two hours. The reaction mixture was then cooled to room temperature, and poured into water to remove sulfolane.

The solid which separated was dissolved in 20 percent aqueous NaOH, filtered and then acidified with concentrated HCl. A white solid precipitated which was filtered off, dried and then refluxed for 1 hour with acetic anhydride.

The product separated on cooling. Gas chromatographic analysis of this residue indicated a major component consisting of 98.3 percent of the total. Mass spectral analysis confirmed its identity to be the desired 4-(4'-nitrophenoxy) phthalic anhydride.

EXAMPLE 2

A mixture of 0.38 parts phenol, 0.71 parts of 4-fluorophthalic anhydride and 0.19 parts of potassium fluoride in 3.8 parts of sulfolane, was heated and maintained at a temperature of about 185°–205° C., with stirring, for a period of about 3 hours, then cooled to room temperature. Gas chromatographic and mass spectral analysis of the reaction mixture indicated 68.9 percent of 4-phenoxyphthalic anhydride.

EXAMPLE 3

The procedure of Example 2 was repeated except that the potassium fluoride replaced with 0.60 parts of cesium fluoride. A 36.9 percent yield of 4-phenoxyphthalic anhydride was detected by GC/MS.

EXAMPLES 4–11

The general procedure of Examples 2 and 3 was repeated in a series of experiments, with variation of reaction conditions and of the particular components of the reaction mixture. The components of the reaction mixture for each example, together with the reaction conditions and the analysis in G.C. area percent are set forth in Table 1 below.

EXAMPLE 12

4-(4'-Bromophenoxy)phthalic Anhydride

To 5.2 parts of 4-bromophenol and 1.7 parts of potassium fluoride was added a solution of 5 parts of 4-fluorophthalic anhydride dissolved in 18.8 parts of sulfolane. The mixture was heated, with stirring, at 190°–195° C. for 4 hours. A GC/MS analysis of the product mixture showed 97.4 (area percent) of 4-(4'-bromophenoxy)phthalic anhydride.

EXAMPLE 13

4-(2'-Trifluoromethylphenoxy) Phthalic Anhydride

Following the general procedure of Example 12, 0.47 parts of α,α,α-trifluoro-o-cresol, 0.23 parts of KF and 0.44 parts of 4-fluorophthalic anhydride in 1.56 parts of sulfolane were heated for 4 hours at 190° C., with stirring. The mixture contained 67 percent (by area) of the above product as identified by GC/MS.

EXAMPLE 14

4-(4'-trifluoromethylphenoxy) Phthalic Anhydride

The procedure of Example 13 was repeated except that in place of α,α,α-trifluoro-o-cresol there was substituted an equivalent amount of the para-isomer. Analysis of the reaction product by GC/MS indicated 68.7 area percent of 4-(4'-trifluoromethyl(phenoxy) phthalic anhydride.

EXAMPLE 15

4-(2',6'-Dimethylphenoxy) Phthalic Anhydride

A solution of 0.44 parts of 4-fluorophthalic anhydride dissolved in 1.56 parts of sulfolane was mixed with 0.37 parts of 2,6-dimethylphenol and 0.23 parts of potassium fluoride. The mixture was heated and maintained with stirring at about 190° C. for about 4 hours. The product, as identified by GC/MS consisted of 63.9 percent (by area) of 4-(2,6-dimethylphenoxy) phthalic anhydride.

EXAMPLES 16–22

Following the general procedure of Examples 12–15, a series of reactions were carried out wherein 4-fluorophthalic anhydride was reacted with various phenols in sulfolane in the presence of potassium fluoride. The phenol reactant, conditions employed and analysis of the reaction product are set forth in Table 2 below.

TABLE 1

| Example Number | 2 | 3 | 4 | 5 | 6 | 7 | 8 | 9 | 10 | 11 |
|---|---|---|---|---|---|---|---|---|---|---|
| Phenol | 0.38 | 0.38 | 0.38 | 0.38 | 0.38 | 0.39 | 0.37 | 0.38 | 0.38 | 0.42 |
| 4-Fluorophthalic Anhydride | 0.71 | 0.71 | 0.71 | 0.71 | 0.71 | 0.71 | 0.72 | 0.71 | 0.73 | 0.72 |
| Potassium Fluoride | 0.19 | — | — | — | — | 0.16 | 0.26 | 0.29 | 0.25 | — |
| Sodium Fluoride | — | 0.12 | — | — | — | — | — | — | — | — |
| Cesium Fluoride | — | — | 0.60 | — | — | — | — | — | — | — |
| Lithium Fluoride | — | — | — | 0.10 | — | — | — | — | — | — |
| Barium Fluoride | — | — | — | — | 0.69 | — | — | — | — | — |
| Sulfolane | 2.5 | 2.5 | 2.5 | 2.5 | 2.5 | 2.5 | — | — | — | 2.5 |
| Dimethyl Formamide | — | — | — | — | — | — | 1.9 | — | — | — |
| N-methyl-pyrrolidone | — | — | — | — | — | — | — | 2.1 | — | — |
| Dimethyl Acetamide | — | — | — | — | — | — | — | — | 1.8 | — |
| Potassium Chloride | — | — | — | — | — | — | — | — | — | 0.35 |
| Total Reaction Time (hrs) | 3.0 | 3.0 | 3.0 | 3.0 | 3.0 | 3.0 | 3.0 | 3.0 | 3.0 | 3.0 |
| Oil Bath Temperature (°C.) | 185–207 | 177–83 | 180–81 | 180–90 | 178–86 | 180 | 150–70 | 165–200 | 180 | 170–85 |
| Reaction Product 4-Phenoxyphthalic anhydride (G. C. Area %) | 68.92 | — | 36.89 | 1.62 | 0.80 | 70.49 | 92.93 | 98.36 | 89.04 | — |

TABLE 2

| Example No. | Phenol Reactant | Conditions Hours | Temperature (°C.) | Product (Major Component) | Reaction Product Analysis (GC (Area % of Major Component) |
|---|---|---|---|---|---|
| 16 | 3-acetamidophenol | 2.5 | 180 | 4-(3'-acetamidophenoxy)phthalic anhydride | 50.0 |
| 17 | 4-acetamidophenol | 2.5 | 180 | 4-(4'-acetamidophenoxy)phthalic anhydride | 66.0 |
| 18 | m-trifluoromethyl phenol | 3.5 | 165–180 | 4-(3'-trifluoromethylphenoxy)phthalic anhydride | 93.3 |
| 19 | p-fluorophenol | 3 | 173–179 | 4-(4'-fluorophenoxy)phthalic anhydride | 85.7 |
| 20 | o-cresol | 4 | 157–188 | 4-(2'-methylphenoxy)phthalic anhydride | 57.0 |
| 21 | p-methoxyphenol | 4 | 157–188 | 4-(4'-methoxyphenoxy)phthalic anhydride | 39.6 |
| 22 | p-cresol | 3 | 170–190 | 4-(4'-methylphenoxy)phthalic anhydride | 75.4 |

EXAMPLE 23

4-(4'-phenylphenoxy) phthalic anhydride

To a solution of 0.66 parts (0.004 mole) of 4-fluorophthalic anhydride in 3 parts of sulfolane, was added 0.68 parts (0.004 mole) of p-phenylphenol and 0.23 parts (0.004 mole) of potassium fluoride. The mixture was heated and maintained at a temperature of about 175°–200°, with stirring for a period of about 5 hours.

The product was analyzed by gas chromatographic and mass spectral techniques.

The procedure was repeated except that the p-phenylphenol was replaced with molar equivalents of various other substituted phenols, with the results as set forth in Table 3, below.

EXAMPLE 42

4-(2'-Methoxy-4'-carboxaldehyde phenoxy) phthalic anhydride

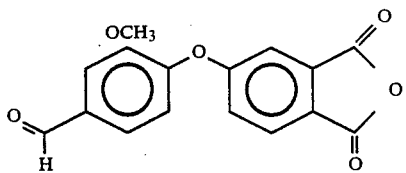

To 0.61 parts of vanillin (2-methoxy-4-carboxaldehyde phenol) and 0.23 parts of potassium fluoride was added a solution of 0.66 parts of 4-fluorophthalic anhydride dissolved in 2.4 parts of sulfolane. The mixture was heated in an oil bath set at 200°–220° C. for about 2.3 hours, with stirring. Analysis of the reaction product by gas chromatography/mass spectrometry, indicated 57.4% of the desired product, 4-(2'-methoxy-4'carboxaldehyde phenoxy) phthalic anhydride.

EXAMPLE 43

4-(3'-Acetoxyphenoxy) phthalic anhydride

As above, 0.61 parts of resorcinol monoacetate, 0.23 parts of potassium fluoride and 0.66 parts of 4-fluoroph-

TABLE 3

| Example | Phenol Reactant | Product (Major Component) | Reaction Product Analysis (GC Area % of Major Component) |
|---|---|---|---|
| 23 | 4 - phenylphenol | 4-(4'-phenylphenoxy)phthalic anhydride | 78.3 |
| 24 | 2 - phenylphenol | 4-(2'-phenylphenoxy)phthalic anhydride | 88.2 |
| 25 | 4 -t-octylphenol | 4-(4'-t-octylphenoxy)phthalic anhydride | 55.8 |
| 26 | 2,6 -difluorophenol | 4-(2',6'-difluorophenoxy)phthalic anhydride | 70.2 |
| 27 | 2,4 -difluorophenol | 4-(2',4'-difluorophenoxy)phthalic anhydride | 81.6 |
| 28 | 2,6 -dichlorophenol | 4-(2',6'-dichlorophenoxy)phthalic anhydride | 27.0 |
| 29 | 2,6 -dibromophenol | 4-(2',6'-dibromophenoxy)phthalic anhydride | 12.4 |
| 30 | 4 - phenoxyphenol | 4-(4'-phenoxyphenoxy)phthalic anhydride | 80.1 |
| 31 | 2,3 -dimethylphenol | 4-(2',3'-dimethylphenoxy)phthalic anhydride | 49.0 |
| 32 | 3,4 -dimethylphenol | 4-(3',4'-dimethylphenoxy)phthalic anhydride | 56.0 |
| 33 | 2 -t-butylphenol | 4-(2'-t-butylphenoxy)phthalic anhydride | 28.0 |
| 34 | 2,6 -di-t-butylphenol | 4-(2',6'-di-t-butylphenoxy)phthalic anhydride | None Formed |
| 35 | 2 -i-propylphenol | 4-(2'-i-propylphenoxy)phthalic anhydride | 56.0 |
| 36 | 2,6-di-i-propylphenol | 4-(2',6'-di-i-propylphenoxy)phthalic anhydride | 18.0 |
| 37 | 2-naphthol | 4-(2'-naphthoxy)phthalic anhydride | 68.0 |
| 38 | 2-cyanophenol | 4-(2'-cyanophenoxy)phthalic anhydride | 49 |
| 39 | 3-cyanophenol | 4-(3'-cyanophenoxy)phthalic anhydride | 63 |
| 40 | 3-N,N-dimethylphenol | 4-(3'-N,N-dimethylphenoxy)phthalic anhydride | 4 |
| 41 | 2,4,6-tribromophenol | 4-(2',4',6'-tribromophenoxy)phthalic anhydride | 2.2 | thalic anhydride dissolved in 3.0 parts of sulfolane gave 10.7% product when heated together, with stirring, for 2.3 hours at 200°–220° C.

What is claimed is:

1. 4-(Methoxy-4'-carboxaldehyde phenoxy)phthalic anhydride.
2. 4-(3'-Acetoxyphenoxy)phthalic anhydride.
3. 4-(2',6'-Dimethylphenoxy)phthalic anhydride.
4. 4-(4'-Phenylphenoxy)phthalic anhydride.
5. 4-(-3'-trifluoromethylphenoxy)phthalic anhydride.
6. 4-(2'-Phenylphenoxy)phthalic anhydride.
7. 4-(4'-t-octylphenoxy)phthalic anhydride.
8. 4-(4'-Phenoxyphenoxy)phthalic anhydride.
9. 4-(2',3'-Dimethylphenoxy)phthalic anhydride.
10. 4-(3',4'-Dimethylphenoxy)phthalic anhydride.
11. 4-(2'-t-butylphenoxy)phthalic anhydride.
12. 4-(2',6'-Di-t-butylphenoxy)phthalic anhydride.
13. 4-(2'-i-propylphenoxy)phthalic anhydride.
14. 4-(2',6'-Di-i-propylphenoxy)phthalic anhydride.
15. 4-(2'-Naphthoxy)phthalic anhydride.
16. 4-(3'-Cyanophenoxy)phthalic anhydride.
17. 4-(3'-N,N-dimethylphenoxy)phthalic anhydride.

* * * * *